| United States Patent [19] | [11] Patent Number: 4,643,897 |
| Gayral et al. | [45] Date of Patent: Feb. 17, 1987 |

[54] METHOD FOR THE TREATMENT OF AMOEBIASIS

[75] Inventors: Philippe G. Gayral, Villejuif; Bernard M. Hublot, Paris, both of France

[73] Assignee: Laboratoires Biocodex, Montrouge, France

[21] Appl. No.: 716,193

[22] Filed: Mar. 26, 1985

[51] Int. Cl.$^4$ .................... A61K 35/72; A01N 63/00
[52] U.S. Cl. ........................................ 424/93; 424/88
[58] Field of Search .................................. 424/88, 93

[56] References Cited

FOREIGN PATENT DOCUMENTS 2096887 3/1972 France .

*Primary Examiner*—Blondel Hazel
*Attorney, Agent, or Firm*—Young & Thompson

[57] ABSTRACT

A method for the treatment of amoebiasis in humans, comprising administering to a human patient suffering from amoebiasis a therapeutically effective amount of yeasts of the genus Saccharomyces. The yeasts are preferably lyophilized, and are administered at a daily dosage level of 0.5–10 g. The species *Saccharomyces boulardii* is preferred.

8 Claims, No Drawings

METHOD FOR THE TREATMENT OF AMOEBIASIS

BACKGROUND OF THE INVENTION

This invention concerns a method for the treatment of amoebiasis, comprising administering yeast of the genus *Saccharomyces*.

Amoebiasis is a parasitic infectious disease due to a protozoan agent, *Entamoeba histolytica* or dysenteric amoeba. It is observed throughout the world, especially in hot humid areas, and particularly in tropical countries that represent the elective area of the amoebic endemia. However, amoebiasis is not unusual even in temperate climates, particularly because of the present large-scale mixing of populations.

The more common form of this disease is intestinal amoebiasis which expresses itself in two different manners:

amoebic dysentery, which expresses itself in severe abdominal pain, frequent stools comprising glairs and blood, with a tendency to chronicity; and chronic amoebic colitis, more usually found in temperate climates, which expresses particularly in a chronic diarrhea with frequent alternate spells of constipation and of a great variety of disorders (such as gastric or hepatic-biliary dyspepsia, neuro-vegetative manifestations and the like), which may last for years even after the amoebae have disappeared.

Amoebae may also attack the liver, and, more seldom, the lungs, so that amoebic hepatitis is a severe form of the disease, Amoebiasis is essentially treated by administration of amoebicides, most of which are quinoline or arsenic derivatives, which are not well tolerated. The nitroimidazoles are effective on tissulary amoebiasis but have insufficient activity on intestinal forms of the disease. In addition, prophylaxis of amoebiasis can hardly be carried out since the de-parasitization of the familiars affected is little effective. Therefore, it would be desirable that a sparingly noxious, easy to use amoebicidal agent be made available.

It is also known that yeasts of the genus *Saccharomyces*, such as *Saccharomyces boulardii* and *Saccharomyces cerevisiae* have been used for a long time in the prevention and the treatment of disorders of the gastro-intestinal tract, particularly diarrhoea or colitis associated with the intake of antibiotics. Such yeasts are generally administered orally, as capsules containing 0.050–0.200 g active ingredient, the daily dosage regimen being usually comprised between 0.100 and 0.400 g for adults.

It has now been found that yeasts of the genus *Saccharomyces*, particularly *Saccharomyces boulardii*, significantly reduce the effect and severity of amoebiasis in rodents, particularly in young rats, whose coacal amoebiasis is recognized as an experimental model of that of the human colon (WOOLFE G., Experimental Chemotherapy vol. 1, ed. R. L. Schnitzer and H. Hawking, 1963, Acad. Press, 422–443).

DETAILED DESCRIPTION OF THE INVENTION

Therefore, the object of this invention is to provide a method for the treatment of amoebiasis in humans, comprising administering a therapeutically effective amount of yeasts of the genus *Saccharomyces*. Preferably, the yeasts administered are kept alive by lyophilization. They may be administered typically at a daily dosage regimen of from 0.5 g to 10 g (based on their weight in lyophilized condition). More particularly, the yeasts used according to this invention belong to the species *Saccharomyces boulardii*.

The yeasts are usefully administered orally, at unit dosages of from 0.500 g to 2.5 g, for example as capsules containing about 0.250 g yeasts or as sachets containing 0.25–2.5 g yeasts. It is understand, however, that other formulations, such as suspensions and other routes of adminsitration may also be used.

A preferred embodiment of the invention comprises a method for treatment of amoebiasis in humans, comprising administering a daily dosage of 0.5–5 g live *Saccharomyces boulardii*.

The following Examples illustrate the invention.

EXAMPLE 1

(a) Biological material

1. Amoebae: *Entamoeba histolytica*, Rahman strain as a mixed culture with procaryotic bacteria. The amibes are cultivated at 37° C. on a two-phase medium (a Ringer solution completed with horse serum covering a coagulated serum slope and rice startch grains) and are associated with bacteriae, particularly *Citrobacter* sp.

The pathogenic power is controlled at monthly intervals, using the test of the amoebic liver abscess in hamsters (see WOOLFE G. above). The amoebae strains are sysmatically re-isolated from the liver and maintained in a culture for some months. Should the activity become reduced, a new strain, which has been more recently isolated from a hamster liver, is used.

2. Yeasts: lyophilized *Saccharomyces boulardii* from: Laboratoires Biocodex (France). The yeasts are rehydrated within a 5% sodium chloride solution and activated by means of a 10 minute thermal shock at 25°–30° C. This suspension containing live yeasts is used extemporaneously.

A variety of *Saccharomyces boulardii* preparations were compared: live yeasts, yeasts sterilized by autoclaving, and ground yeasts, selecting, for the oral treatment, a dosage of 1.5 g/kg/day.

3. Rats "C D" (SPRAGUE-DAWLEY, Laboratories Charles River, France). The animals used are weaning young rats of either sex, having a body weight of 35–40 g. They are fed a common powdered milk, apples, and are given water *ad libitum*. On the day prior to the experiment, they are kept on a water-diet, after having been administered 0.1 ml/kg body weight of a saturated magnesium sulfate solution which induces a certain intestinal emptiness.

(b) Inoculation of the amoeba

The above rats are anesthetized by intraperitoneal injection of 25 mg/kg body weight of sodium pentobarbital. After laparotomy, the caecum is made free, slightly irritated by rubbing, and into it are injected about 500,000 trophozoites of *Entamoeba histolytica* under a volume of about 0.5 ml. The surgical wound is sutured in two planes, muscular and cutaneous.

The young rats recover within 2 or 3 hours, and may again be grouped in breeding cages where they continue being fed powdered milk, apples and water. About 10% of the animals die as a consequence of the inoculation within the first 24 hours.

(c) Treatment of the amoebic young rats

The yeast is still administered at a dosage of 1.5 g/kg/day, suspended in a 5% sodium chloride solution in distilled water. The treatment is conducted using a gastric cannula, by administration of two daily doses of 0.2 ml per young rat at 10 A.M. and at 6 P.M. The reference animals are adminstered only the saline solution.

1. Curative test. The young rats are administered the yeasts the day after inoculation of the amoeba: this treatment lasts four days (D2 to D5), but could be shortened as a function of the results. Such tests are conducted comparatively with live, sterilized, or ground yeasts, for a four day treatment period.

2. Preventive test: the yeast is administered from one to three days prior to inoculation.

(d) Quantitative evaluation of the degree of infection

The animals are sacrificed on the 6th day (D6) by means of an extended anesthesia (ether) and are autopsied blind. The caecum is made free, slit lengthwise and examined.

The severity of the amoebic involvement is evaluated by means of an index directly inspired by Woolfe's index with, however, greater consideration being given to tissue reaction factors:

appearance of the caecum: normal or retracted, and thickness of the wall (normally thin);

contents of the caecum: normally granular and firm, particularly the inspection for mucus at the wall-contents interface;

the presence of amoebae: detected by direct microscopic examination of the product obtained by scraping the caecal wall, and of the mucus, and after cultivation.

According to its pathological condition, each animal is assigned a severity index from 0 (amoeba-free) to 5 (severely affected).

The results are presented according to classes of severity, that allows to discuss of the dividing up of the animals according to the treatments between different classes, by the statistical test of the "square-chi":

Index 0: amoeba-free animals (cured or not infected)
Index 1-2-3: animals only slightly affected
Index 4-5: severely affected animals.

(e) Results

The results of the different experiments are grouped according to test type in the following Table.

TABLE

| INDICES | Live yeasts 1st experiment | | live yeasts 2nd experiment | |
| --- | --- | --- | --- | --- |
| | CONTROLS | TREATED | CONTROLS | TREATED |
| 0 (CURED) | 1 | 6 | 1 | 10 |
| 1-2-3 (SLIGHTLY AFFECTED) | 0 | 3 | 7 | 2 |
| 4-5 (SEVERELY AFFECTED) | 8 | 1 | 5 | 1 |
| TOTAL ANIMALS | 9 | 10 | 13 | 13 |
| STATISTICAL MEANING | $X^2 = 12,01$ p 0,01 | | $X^2 = 12,81$ p 0,01 | |

In the curative activity tests, the effect of the treatment is clear at two levels: increase of the number of amoeba-free animals and considered as having been cured, and decrease of the severely affected animals and of higher index which number 8 out of 9 in the controls and number 1 out of 10 in the treated animals.

Complementary investigation showed that this significant effect of the yeast has also been found with the autoclaved yeast, although to a lower degree; the ground yeast exhibits a low activity with a non-significant decrease of the number of highly affected young rats; the treatment time required for the curative activity at a daily dosage regimen of 1.5 g/kg/day is of 3 days.

In the preventive activity tests, the experiment conducted over 2 or 3 days shows a moderate effect of the yeast.

On the other hand, there was not observed any toxicity assignable to any one of the three materials administered, either through death of the rodents or during the treatments.

In the young rat, live *Saccharomyces boulardii* yeasts possess an undeniable effect on the populations of trophozoites of *Entamoeba histolytica* and on the caecal pathology they induce. Since the lesion of the caecal wall is recognized as being closely similar to the lesion of the human colon, the results of this pharmacological investigation appear to us to be a priori in favour of the use of *Saccharomyces* yeasts in the control of amoebiasis in humans.

EXAMPLE 2

Capsule containing:
lyophilized cells of *Saccharomyces boulardii*: 250 mg
magnesium stearate: 3 mg

We claim:

1. Method for the treatment of amoebiasis in humans, comprising administering to a human patient suffering from amoebiasis a therapeutically effective amount of yeasts of the genus *Saccharomyces*.

2. Method as claimed in claim 1, wherein the yeasts administered are lyophilized.

3. Method as claimed in claim 1, wherein the yeasts are administered at a daily dosage regimen of 0.5–10 g.

4. Method as claimed in claim 1, wherein the yeasts belong to the species *Saccharomyces boulardii*.

5. Method as claimed in claim 1, wherein the yeasts are administered in unit dosages for oral administration containing 0.250–2.5 g yeasts.

6. Method as claimed in claim 5, wherein the unit dosages are formulated as capsules containing about 0.250 g of yeasts.

7. Method as claimed in claim 5, wherein the unit dosages are formulated as sachets containing about 0.250–2.5 g of yeasts.

8. Method for the treatment of amoebiasis in humans, comprising administering to a human patient suffering from amoebiasis a daily dosage of 0.5–5 g live *Saccharomyces boulardii*.

* * * * *